(12) United States Patent
Renisch et al.

(10) Patent No.: US 10,870,017 B2
(45) Date of Patent: Dec. 22, 2020

(54) FALL-BACK SOLUTION FOR UNCERTAIN REGIONS IN MRCAT IMAGES

(71) Applicant: KONINKLIJKE PHILIPS N.V., Eindhoven (NL)

(72) Inventors: Steffen Renisch, Eindhoven (NL); Nicole Schadewaldt, Eindhoven (NL); Sven Prevrhal, Eindhoven (NL); Heinrich Schulz, Eindhoven (NL); Thomas Blaffert, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 277 days.

(21) Appl. No.: 15/559,210

(22) PCT Filed: Mar. 18, 2016

(86) PCT No.: PCT/EP2016/056072
§ 371 (c)(1),
(2) Date: Sep. 18, 2017

(87) PCT Pub. No.: WO2016/150888
PCT Pub. Date: Sep. 29, 2016

(65) Prior Publication Data
US 2018/0071550 A1    Mar. 15, 2018

(30) Foreign Application Priority Data
Mar. 20, 2015    (EP) .................... 15160158

(51) Int. Cl.
*A61N 5/10* (2006.01)
*A61B 5/055* (2006.01)
(Continued)

(52) U.S. Cl.
CPC .......... *A61N 5/1039* (2013.01); *A61B 5/0033* (2013.01); *A61B 5/055* (2013.01);
(Continued)

(58) Field of Classification Search
CPC .............. A61N 5/1039; G01R 33/4828; G01R 33/5608; G06T 7/0012; G06T 2207/30008; G06T 2207/10088; A61B 6/5229
(Continued)

(56) References Cited

U.S. PATENT DOCUMENTS 8,718,232 B2    5/2014    Delso
10,223,794 B2    3/2019    Schadewaldt
(Continued)

FOREIGN PATENT DOCUMENTS

WO    2014161766 A1    10/2014

OTHER PUBLICATIONS

Halle et al "Evaluation of Dixon Based Soft Tissue and Bone Classification in the Pelvis for MR Only Based Radiation Therapy Planning" Proceedings of the annual conference of the international society of magnetic resonance in medicine (ISMRM) 2014. Abstract #4238 Proc. Intl. Soc. Mag. Reson. Med. 22 (2014).
(Continued)

*Primary Examiner* — Samuel G Gilbert
(74) *Attorney, Agent, or Firm* — Sherry Austin

(57) ABSTRACT

The present invention teaches a method and system for computing an alternative electron density map of an examination volume. The processing system is configured to compute a first electron density map using a plurality of imaging data, compute a second electron density map, wherein the second electron density map is a simplified version of the first electron density map, and compute the alternative electron density map, using the first electron density map and the second electron density map.

15 Claims, 3 Drawing Sheets

(51) Int. Cl.
 A61B 5/00 (2006.01)
 G01R 33/56 (2006.01)
 G01R 33/48 (2006.01)
 G01R 33/54 (2006.01)
(52) U.S. Cl.
 CPC .............. *A61B 5/45* (2013.01); *A61B 5/7278* (2013.01); *A61N 5/1031* (2013.01); *G01R 33/4812* (2013.01); *G01R 33/5608* (2013.01); *A61B 5/0035* (2013.01); *A61B 5/748* (2013.01); *A61B 2576/00* (2013.01); *G01R 33/543* (2013.01)
(58) Field of Classification Search
 USPC ........................................................... 600/1
 See application file for complete search history.

(56) References Cited

U.S. PATENT DOCUMENTS

| | | |
|---|---|---|
| 10,539,682 B2 | 1/2020 | Jacobs |
| 2012/0157746 A1 | 6/2012 | Meltsner |
| 2013/0039558 A1 | 2/2013 | Balter et al. |
| 2014/0296696 A1 | 10/2014 | Remmele et al. |
| 2015/0117595 A1 | 4/2015 | Flohr |
| 2016/0216352 A1 | 7/2016 | Eggers |
| 2018/0085080 A1* | 3/2018 | Requardt ........... G01R 33/4812 |

OTHER PUBLICATIONS

Johansson et al "CT Substitiute Derived From MRI Sequences With Ultrashort Echo Time" Medical Physics 38(5) May 2011.

Hofmann et al "MRI-Based Atenuation Correction for Whole Body PET-MRI Quantitative Evaluation of Segmentation and Atlas Based Methods" The Journal of Nuclear Medicine, vol. 52, No. 9, Sep. 1, 2011 p. 1392-1399.

Delso Gaspar et al "The Effect of Limited MR Field of View in MR/PET Attenuation Correction" Medical Physics, vol. 37, No. 6, May 20, 2010 p. 2804-4812.

Shu-Hui Hsu et al "Investigation of a Method for Generating Synthetic CT Models From MRI Scans . . " Physics in Medicine and Biology, vol. 58, No. 23, Nov. 11, 2013, p. 8419-8435.

Greer, "A Magnetic Resonance Imaging-Based Workflow for Planning Radiation Therapy for Prostate Cancer" MJA vol. 194, No. 4 Feb. 21, 2011 p. S24-S27.

Sjoberg, "Dosimetric and Geometric Evaluation of MRI As the Only Imaging Modality for the Radiotheraphy Treatment Process of Localized Prostate Cancer" Disertation, Lund University, Sweden 2010.

Korhonen, "Electron Density Conversion From Magnetic Resonance Image Intensity Values for MRI-Based Radiotherapy Treatment Planning of Prostate Cancer" Physics Days, 2013, AALTO University Finland.

Wang, "MRI-Based Treatment Planning With Electron Density Information Mapped From CT Images: A Preliminary Study" Technology in Cancer Research and Treatment, vol. 7, No. 5, Oct. 2008 p. 341-347.

Kapanen et al "T1/T2 Weighted Mri Provides Clinically Relevant Pseudo-CT Density Data for the Pelvic Bones in MRI-Only Based Radiotherapy Treatment Planning" Acta Oncologica, 2013, 52: p. 612-618.

Jonsson et al, "Treatment Planning Using MRI Data: An Analysis of the Dose Calculation Accuracy for Different Treatment Regions" Radiation Oncology, 2010 5: p. 62.

* cited by examiner

FALL-BACK SOLUTION FOR UNCERTAIN REGIONS IN MRCAT IMAGES

CROSS REFERENCE TO RELATED APPLICATIONS

This application is a U.S. national phase application of International Application No. PCT/EP2016/056072, filed on Mar. 18, 2016, which claims the benefit of EP Application Serial No. 15160158.0 filed on Mar. 20, 2015 and is incorporated herein by reference.

FIELD OF THE INVENTION

The present invention pertains to the field of magnetic resonance (MR) imaging for radiotherapy planning. More specifically, the present invention relates to a system and method to computing an alternative electron density map of an examination volume.

BACKGROUND OF THE INVENTION

Computed Tomography (CT) is used in the field of radiation therapy planning, whereby information gathered by CT imaging are directly related to the electron density (ED) and can therefore be used as a basis for the computation of the radiation dose during treatment simulation.

In order to reduce radiation exposure, it has been proposed to generate an electron density (ED) map of a patient to be examined by way of Magnetic Resonance (MR) imaging. Magnetic resonance imaging (MRI) uses strong magnetic fields and radio waves to produce cross-sectional images of organs and internal structures in the body. Because the signal detected by an MRI machine varies depending on the water content and local magnetic properties of a particular area of the body, different tissues or substances can be distinguished from one another in the study image.

An electron density map may be derived from the magnetic resonance signals and such an electron density map derived from magnetic resonance imaging is called a MR-CAT image ('MR-Calculated Attenuation'). Such an image may also be named a 'synthetic CT image' because it represents similar information as a computed-tomography images, while no harmful irradiation with x-rays is needed. For magnetic resonance-based radiotherapy planning, the dose distribution is computed on basis of information gathered from the MR-CAT image.

Due to the physics of the image acquisition, magnetic resonance intensities do not uniquely correspond to electron density. Hence, electron density maps cannot be derived from an MR image by a simple lookup operation, as is commonly done when estimating these electron density maps from CT images. A first approach for creating a CT-like image from the MR image is described in "Evaluation of Dixon based Soft Tissue and Bone Classification in the pelvis for MR only based Radiation Therapy Planning", Michael Helle, Nicole Schadewaldt, et al., abstract accepted at ISMRM 2014. This first approach relies on bulk density assignment to a number of pre-defined tissue classes. Other approaches include modelling CT value dependency from multi-dimensional MR information, as taught in the scientific paper entitled "CT substitute derived from MRI sequences with ultrashort echo time", Adam Johansson, Mikael Karlsson and Tufve Nyholm, in Medical Physics 38 (5) May 2011.

However, the MR-CAT image obtained by these approaches may be an inaccurate electron density-map equivalent, e.g. due to image artifacts from the MR acquisition or from the image processing. This might subsequently lead to a difference in the computed dose distribution. It is difficult to estimate the actual influence of the MR-CAT artifact on the dose distribution. Creating estimated electron density maps from MR images is therefore an issue.

Considering the above, it is an object of the invention to provide a system and a method for an improved electron density map from magnetic resonance imaging.

SUMMARY OF THE INVENTION

According to the invention, the object is achieved by a processing system with the features of claim 1, a planning system with the features of claim 5, a method with the features of claim 6, method with the features of claim 10. Preferred embodiments are defined in the respective dependent claims.

In one aspect of the disclosure, a processing system is provided for computing an alternative electron density map of an examination volume. The processing system is configured to compute a first electron density map using a plurality of imaging data, compute a second electron density map, wherein the second electron density map is a simplified version of the first electron density map, and compute the alternative electron density map, using the first electron density map and the second electron density map. The present disclosure therefore teaches to replace the electron density map obtained with unknown errors by an alternative electron density map. The present invention concerns the computation of an electron density (ED) map, notably by way of magnetic resonance imaging. The computation of the present invention has two stages. To start with, a first ED-map is computed. A second ED map is computed that is a simplified version of the first ED-map. Notably the second EM map is simplified in that it represents the same part of the anatomy as the first ED map, but contains less details. Generally, the second ED map is less susceptible to artefacts. Then, according to the invention the second ED map is employed together with the first ED map to compute an alternative ED map. In the preferred implementation of the invention, the alternative ED map is formed by replacing artefact areas of the first ED map by the (data of) the second (simpler) ED map. An insight of the present invention is that the alternative ED map is more reliable, e.g. for radiation therapy planning, than the first ED map. The replacement by less details of artefact regions appears to be favourable and does not require the efforts to remove or avoid the artefact altogether in the first ED map.

In another aspect of the disclosure, the processing system is configured to replace, in one ore more artefact areas, the first electron density map by the second electron density map, to obtain the alternative electron density map. The invention therefore proposes using a simplified electron density map which is less susceptible to artefacts. The alternative electron density map may lead to errors in a dose distribution, however these errors are known to be within clinical tolerance limits. In other words, the one or more artefact areas with unknown influence on the dose distribution may be replaced by an artefact with an acceptable influence on the dose distribution.

In a further aspect of the system, a user interface system is provided and is configured to display the first electron density map, and the user interface system comprising a user input system allowing a user to input user data identifying and delimiting the one or more artefact aeras on the first electron density map. Hence, a user can interactively analyse the first electron density map and decide which zones are to be considered as artefact areas.

In an aspect, the second electron density map corresponds to a contour of the first electron density map and is filled with a uniform value, in particular the uniform value being an equivalent water density. A contour filled with a uniform value is an example of a simplified first electron density map which is easy to compute and leads to a reasonable error.

The present disclosure also proposes a planning system for computing a dose radiation distribution. The planning system comprises a processing system as described above. The planning system is configured for computing a first electron density map using a plurality of imaging data, a second electron density map and an alternative electron density map, the alternative electron density map being computed using said first and second electron density maps. The planning system further comprises a radiation therapy planning system configured to compute a first dose radiation distribution using the first electron density map and to recompute a second dose distribution using the alternative electron density map.

The present invention also teaches a method of computing an alternative electron density map of an examination volume, comprising the step of computing a first electron density map using a plurality of imaging data, computing a second electron density map, wherein the second electron density map is a simplified version of the first electron density map, and computing the alternative electron density map (84) using the first electron density map (80) and the second electron density map (82).

In one aspect of the disclosure, the method comprises the step of replacing, in one ore more identified artefact areas, the first electron density map by the second electron density map, to obtain the alternative electron density map. The method therefore suggests replacing unknown errors by errors which are known to be acceptable.

In a further aspect of the disclosure, the method comprises displaying the first electron density map and obtaining user input data identifying the one ore more artefact areas. This allows a user to asses, according to his judgement, whether one or more zones of the first electron density map are to be considered as artefacts and to delineate these one or more artefact areas.

In an aspect of the disclosure, the method comprises assigning to the second electron density map an uniform density value, in particular a water equivalent density value. A uniform density value such as a water equivalent density value may be known to lead to acceptable errors. A uniform value further is easier to handle for the computation of the alternative electron density map.

The present disclosure also proposes a method of computing a dose radiation distribution comprising the steps of computing a first electron density map, computing a first dose radiation distribution using the first electron density map, computing an alternative density map using a method as described above and/or a system as described above, and computing a second dose distribution using the alternative electron density map. The method therefore allows the user to assess the potential effect of the one or more artefact areas on the dose distribution.

The present disclosure further proposes computer program product comprising control logic stored therein for causing a computer to execute instructions that enable a processor to carry out the steps of the proposed methods.

The present disclosure also proposes a computer program product comprising computer means configured to compute a first electron density map using a plurality of imaging data, compute a second electron density map, wherein the second electron density map is a simplified version of the first electron density map, and compute the alternative electron density map, using the first electron density map and the second electron density map.

DETAILED DESCRIPTION OF THE FIGURES

These and other aspects of the invention will become apparent from and elucidated with reference to preferred embodiments described hereinafter with reference to the accompanying drawings, wherein:

FIG. 1 shows a system 1 for estimating an electron density map of an examination volume V. The system 1 is further adapted to compute a dose distribution based on the estimated electron density map.

DETAILED DESCRIPTION OF THE EMBODIMENTS

Figure 1:
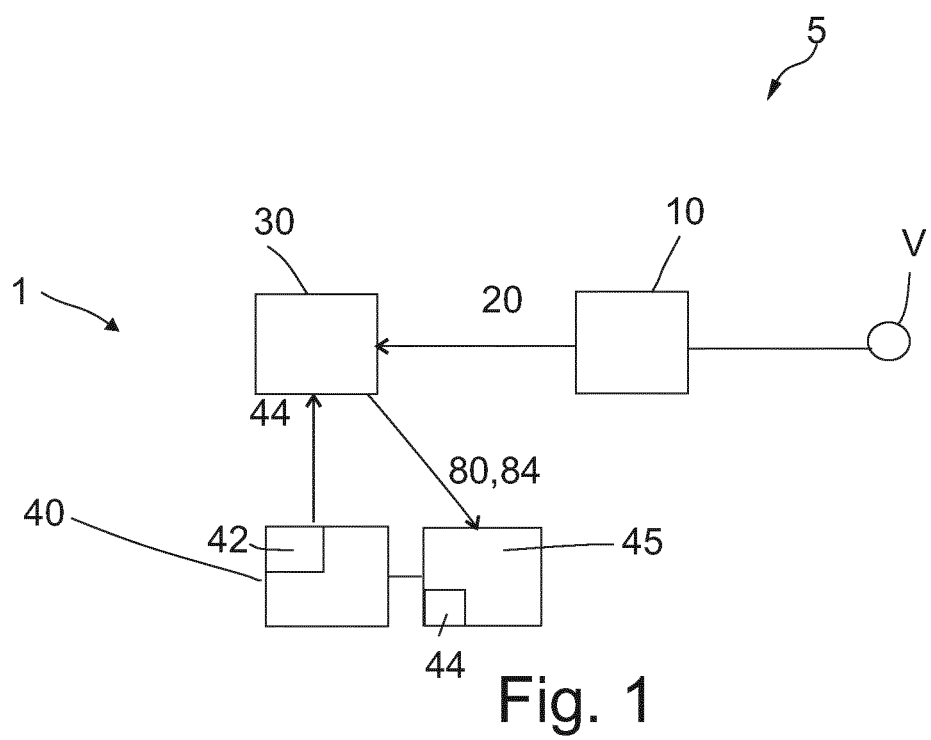
FIG. 1 is a block diagram of a system according to a preferred embodiment of the invention.

To this end, the system 1 comprises an imaging system 10 for acquiring a plurality of image data 20 for acquiring a special distribution of a physical property inside the examination volume. The imaging system 10 is in the described embodiment a Magnetic Resonance (MR) imaging system, as is known in the art. In this case the physical property are magnetic resonance intensities. However, the imaging system may be another type of imaging system whose imaging data can be used for estimating an electron density map.

The system 1 further comprises a processing system 30 configured to process the plurality of image data 20. The processing system 30 is configured to generate a first electron density map 80 based on the acquired plurality of image data 20. The first electron density map 80 shows internal structure of bones and soft tissues. The first electron density map 80 may be computed using computing techniques known in the art.

Figures 3A, 3B:
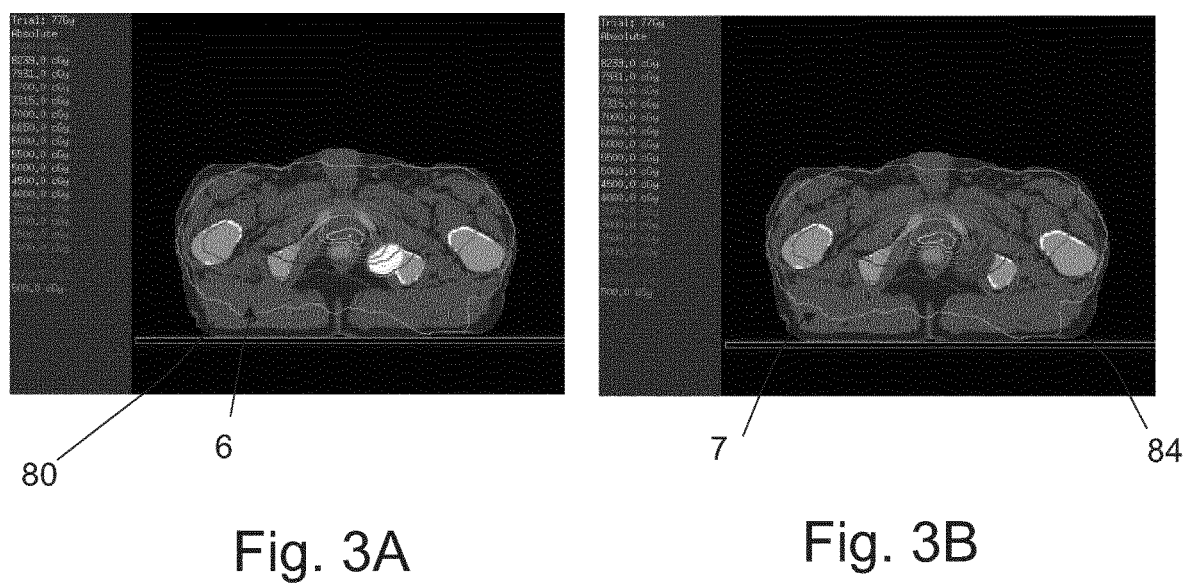
FIG. 3A shows a first image density map and corresponding dose distribution and FIG. 3B shows an alternative image density map and corresponding dose distribution obtained with the system of FIG. 1 and method of FIG. 2.

An example of first electron density map 80 is shown on FIG. 3A. The skilled person will understand that the first electron density map 80 may be computed to have a detail level as high as possible using the imaging system 10 and the computation imaging techniques as know in the art. As explained in the introductory part, the first electron density map 80 corresponds to a MR-CAT image ('MR-Calculated Attenuation'), which may have one or more zones which are identified as being artefact areas 90. In the example of FIG. 3A, the first electron density map 80 has one artefact area 90 comprising an artefact with artefact values 91 and its neighborhood with neighborhood values 92, shown as a bright spot on FIG. 3A. This artefact area 90 may result from the magnetic resonance acquisition or from assignment errors during the processing of the plurality of imaging data and the computing of the first electron density map 80.

The processing system 30 is further configured to generate a second electron density map 82. The second electron density map 82 is a simplified electron density map in comparison with the first electron density map 80, having less level of details but fewer risks of artefacts. In the described embodiment, the second electron density map 82 may represent a contour 92 of the first electron density map 80. The second electron density map 82 may be filled with a uniform density value 93. An example of second electron density map 82 is shown on FIG. 3B. In this example, the second electron density map 82 represents a segmented body outlined and filled with water equivalent density values. This is a non limiting example and other density equivalent values may be used.

The processing system 30 is further configured to derive a third electron density map 84 using the first electron density map 80 and the second electron density map 82. More precisely, the processing system 30 is configured to replace, in the one ore more artefact areas 90 identified in the first electron density map 80, the first electron density map 80 by the second electron density map 82, to obtain a correlated third electron density map 84. In other words, the artefact with artefact values 91 and its neighborhood with neighborhood values 92 in the first electron density map 80 are replaced by the second electron density map density values 93 from the second electron density map 82 in the identified artefact areas. The second electron density map density values 93 are replacement values 93.

A user interface system 40 is provided in the system 1 and is configured for an interactive display to a user. The user interface system 40 may be integrated within the processing system 30 or may be a secondary computing device.

The user interface system 40 is configured to display at least one of the first electron density map 80, the second electron density map 82, and the third electron density map 84.

The user interface system 40 is configured with an input system 42 adapted to allow a user inputting identification data 44 identifying the one or more artefact areas 90 on the first electron density map 80. For example, the user may draw on the display, as identification data 44, an artefact contour of the one or more artefact areas 90, using a pen type device. Other input system 42 may include for example seed-placement and region growing, a paintball, live-wire to encircle the region, placing a ball in the region.

The user may rely on his professional experience to identify and delimit those regions on the first electron density map 80 which are considered to be artefacts or on threshold values provided for his ease or input into the image processing system so as to identify and delimit artefact areas.

The processing system 30 may configured to identify and delimit the regions witch are considered to be artefact areas. For example, the one ore more artefact areas 90 may be detected by a size threshold on cortical bone segments in the body. The processing system 30 may take into account a relation between detected tissue types in image and use said relation as a validity measure to indicate artefacts. An example of such a relation can be a cortical bone fraction in a bone. A method using minimum and maximum threshold values may be used to delimit the one or more artefact areas.

The processing system 30 is configured to use the identified one or more artefact areas 90 in the first electron density map 80 and replace the first electron density map 80 by the second electron density map 82 in the identified one or more artefact areas 90, resulting in the third electron density map 84.

The third electron density map 84 is therefore artefact free or has at least a deviation with respect to the actual density values of the examination volume in the identified artefact areas 90 which is smaller than a deviation with respect to the actual density values resulting from the artefact values 91. In other words, the processing system 30 is adapted to replace the identified artefact areas 90 with unknown errors with regions showing a known and acceptable error. The third electron density map 84 is an alternative electron density map, which can be used for radiation therapy planning for example.

A radiation therapy planning system 45 is configured to compute a radiation dose distribution for the imaged volume using one of the first electron density map 80 or the third electron density map 84. In particular, the radiation therapy planning system 45 is configured to compute a first radiation dose distribution 6 for the imaged volume using the first electron density map 80 and a second radiation dose distribution 7 for the imaged volume using the third electron density map 84.

The first radiation dose distribution 6 may be displayed and superimposed on the first electron density map 80, as seen on FIG. 4A. The second radiation dose distribution 7 may be displayed and superimposed on the third electron density map 84 (FIG. 4B.

The images showing the first dose distribution 35 computed on the first electron density map 80 or the second dose distribution 37 computed on the third electron density map 84 may be displayed by the interactive display 40 or by a secondary display 44.

The images showing the first dose distribution 35 computed on the first electron density map 80 or the second dose distribution 37 computed on the third electron density map 84 may be displayed simultaneously on separate display zones of the interactive display 40 or by a secondary display 44.

The skilled person will understand that the present invention therefore proposes replacing the MR-CAT image in certain areas, e.g. areas marked by the user as implausible, by patches from another ED map that in general might show larger deviations to the true ED map, but is known to give acceptable results for the treatment dose computation. In other words, regions with an unknown error are replaced with regions showing a known and acceptable error in the dose distribution.

Another advantage of the present system is that the user may assess the potential effect of the artifact on the dose distribution, by varying the identified one or more artefact areas.

The processing system 30 and the radiation therapy planning system 45 may be implemented using any type of computing device having one or more computer processors.

Figure 4:
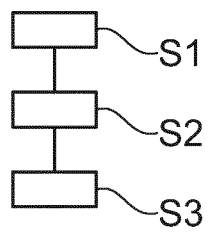
FIG. 4 shows a method computing an alternative electron density map according to an aspect of the disclosure.

FIG. 4 shows a method of computing an alternative electron density map or MR-CAT image according to an aspect of the disclosure. The method is described with reference to the system of FIG. 1.

In a first step S1, the processing system 30 uses the plurality of imaging data to compute a first electron density map 80. The plurality of imaging data may be acquisition data obtained from a Magnetic resonance imaging system. The first electron density map 80 corresponds to an original MR-CAT image showing the best detail level possible. The fist electron density map 80 may have one or more zones which are considered to be implausible and are therefore considered to be artefact areas 90.

The artefact areas may be identified and marked-up by the user visualizing on the user interface system 40 the the first electron density map 80. For example, the user may input by means of a pen a contour delimiting the one or more artefact areas 90 on the first electron density map 80. The identifying and delimiting step can also be performed automatically by a suitable image processing system and software. The processing system 30 may for example use a relation between detected tissue types in image as a validity measure to indicate artefacts. An example of such a relation can be a cortical bone fraction in a bone The processing system 30 may use any computing method known in the art to compute an MR-CAT image based on the imaging data acquired by magnetic resonance measurements.

Figures 2A, 2B:
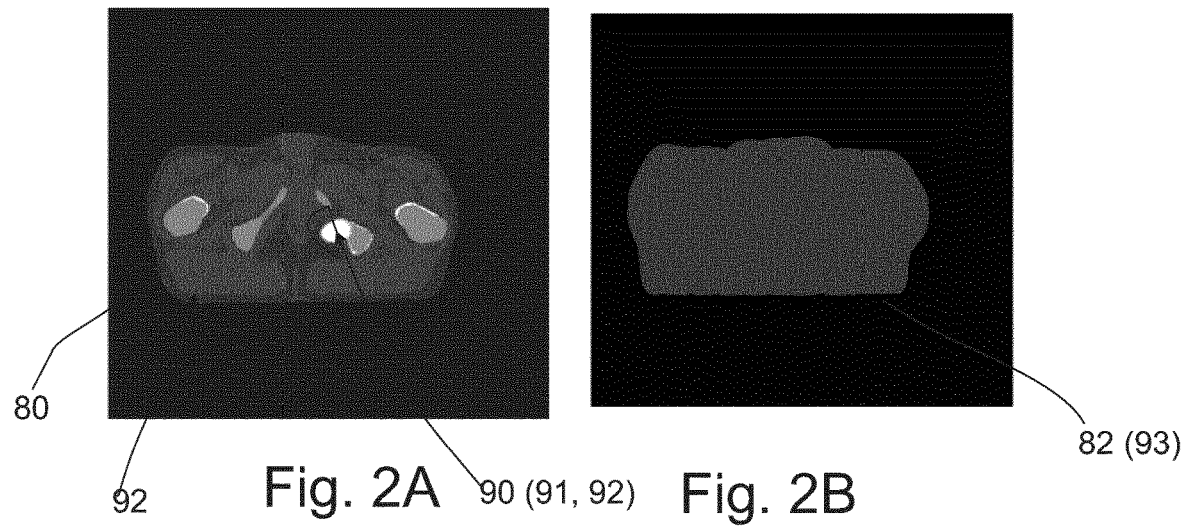
FIGS. 2A and 2B show image density maps obtained with the system of FIG. 1.

In a second step S2, the processing system computes a second electron density map 82, having less details than the first electron density map 80. In other words the second electron density map 82 is a simplified version of the first electron density map 80. An example is shown on FIG. 2B, where the second electron density map 82 corresponds to a simplified first electron density map 80, in which only the body outline is segmented and filled with uniform values. For example, water-equivalent density values may be used.

This step S2 is more robust against image artifacts, on the other hand the deviation from the true density map will generally be larger compared to the original MR-CAT image.

The steps S1 and S2 may be performed in parallel or one after the other. The second electron density map 82 may be computed using the plurality of imaging data. In an alternative aspect of the invention, the second electron density map 82 may be derived from the first electron density map 80. For example, the processing system 30 may derive a contour of the first electron density map and fill the first electron density map with other density values, to come up with the second electron density map 82. The second electron density map 82 is generated by setting a maximum threshold on the first electron density map 80 and by setting any density values above this maximum threshold to with the other density value. A preferred other density value is a density value of water.

In a third step S3, the processing system 30 computes the alternative electron density map 84 using the first electron density map 80 and the second electron density map 82. The processing system 30 replaces, in the one ore more artefact areas 90, the first electron density map 80 by the second electron density map 82, to obtain the alternative electron density map 84.

Figure 5:
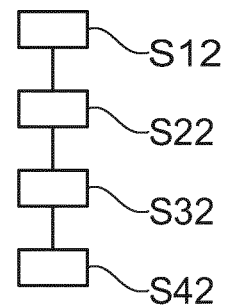
FIG. 5 shows a radiation planning method according to one aspect of the disclosure.

FIG. 5 shows a workflow of a method of computing a dose radiation distribution in one aspect of the disclosure. The method is described with reference to the system described on FIG. 1.

In a first step S21, a first electron density map 80 is computed using the imaging data obtained by magnetic resonance techniques or similar techniques. A first dose radiation distribution 6 is computed using the first electron density map and is displayed together with the first electron density map.

In a second step S22, an alternative density map 84 is computed using the method described with reference to FIG. 4. Using the alternative density map 84, a second dose distribution 7 is computed. The second dose distribution 7 is displayed together with the alternative density map (84).

It will be apparent that the second dose distribution 7 is generated with an acceptable error, instead of the first dose distribution 6 which is generated with an unknown error due to the artefact areas 90 in the first electron density map 80. Additionally, the teachings of the present disclosure allows the user to assess the potential effect of the artifact on the dose distribution.

This invention is applicable to RT planning systems that use MR-based density maps, e.g. Pinnacle or a potential solution for MR-based RT planning. In addition it could be applied also to the PET reconstruction on PET/MR systems.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more features of other embodiments, as may be desired and advantageous for any given particular application. From the above description of the invention, those skilled in the art will perceive improvements, changes and modifications. Such improvements, changes and modifications within the skill of the art are intended to be covered by the appended claims. Any reference signs in the claims do not limit the scope of the invention. The term "comprising" is to be understood as not excluding other elements or steps and the term "a" or "an" does not exclude a plurality.

LIST OF REFERENCE NUMERALS

1: system
6: first dose distribution
7: second dose distribution
10: imaging system
20: plurality of image data
30: processing system
40: user interface system
42: user input
44: secondary display
80: first electron density map
82: second electron density map
84: third electron density map
90: artefact zone
91: density value artefact
92: density value neighborhood
93: replacement density value
95: contour

The invention claimed is:

1. A processing system for computing an alternative electron density map of an examination volume, the processing system configured to:
   compute a first electron density map using a plurality of imaging data,
   compute a second electron density map, wherein the second electron density map is a simplified version of the first electron density map, and
   compute the alternative electron density map, using the first electron density map and the second electron density map.

2. The processing system according to claim 1, wherein the processing system is configured to replace, in one or more artefact areas, the first electron density map by the second electron density map, to obtain the alternative electron density map.

3. The processing system according to claim 1, comprising a user interface system, the user interface system being configured to display the first electron density map, and the user interface system comprising a user input system for a user to input user data identifying and delimiting the one or more artefact areas on the first electron density map.

4. The processing system according to claim 1, wherein the second electron density map corresponds to a contour of the first electron density map and is filled with a uniform value.

5. The processing system according to claim 4, wherein the uniform value is an equivalent water density value.

6. A method of computing an alternative electron density map of an examination volume, the method comprising:
   computing a first electron density map using a plurality of imaging data,
   computing a second electron density map, wherein the second electron density map is a simplified version of the first electron density map, and
   computing the alternative electron density map using the first electron density map and the second electron density map.

7. The method according to claim 6, further comprising:
   replacing, in one or more identified artefact areas, the first electron density map by the second electron density map, to obtain the alternative electron density map.

8. The method according to claim 6, comprising displaying the first electron density map and obtaining user input data identifying the one or more artefact areas.

9. The method according to claim 6, comprising assigning to the second electron density map an uniform density value.

10. The method according to claim 9, wherein the uniform value is an equivalent water density value.

11. A computer program product comprising control logic stored on a non-volatile computer readable medium for causing a computer to execute instructions that enable a processor to carry out the steps of the method of claim 6.

12. A method of computing a dose radiation distribution computing a first electron density map,
   computing a first dose radiation distribution using the first electron density map,
   computing an alternative density map using a method according to claim 6, and
   computing a second dose distribution using the alternative electron density map.

13. A computer program product comprising control logic stored therein for causing a computer to execute instructions that enable a processor to carry out the steps of the method of claim 12.

14. A planning system for computing a dose radiation distribution comprising:
   a processing system according to claim 1, configured for computing a first electron density map using a plurality of imaging data, a second electron density map and an alternative electron density map, the alternative electron density map being computed using said first and second electron density maps, and
   a radiation therapy planning system configured to compute a first dose radiation distribution using the first electron density map and to recompute a second dose distribution using the alternative electron density map.

15. A computer program product comprising computer means configured to:
   compute a first electron density map using a plurality of imaging data
   compute a second electron density map, wherein the second electron density map is a simplified version of the first electron density map; and
   compute an alternative electron density map, using the first electron density map and the second electron density map.

* * * * *